(12) United States Patent
Martin

(10) Patent No.: US 6,884,071 B2
(45) Date of Patent: Apr. 26, 2005

(54) MIXING CAPSULE

(75) Inventor: Mathias Martin, Deggendorf (DE)

(73) Assignee: 3 M ESPE AG, Seefeld (DE)

( * ) Notice: Subject to any disclaimer, the term of this patent is extended or adjusted under 35 U.S.C. 154(b) by 77 days.

(21) Appl. No.: 10/204,246

(22) PCT Filed: Feb. 15, 2001

(86) PCT No.: PCT/EP01/01647
§ 371 (c)(1),
(2), (4) Date: Feb. 14, 2003

(87) PCT Pub. No.: WO01/62176
PCT Pub. Date: Aug. 30, 2001

(65) Prior Publication Data
US 2004/0011815 A1 Jan. 22, 2004

(30) Foreign Application Priority Data
Feb. 21, 2000 (DE) .......................... 100 07 580

(51) Int. Cl.⁷ .............................. A61C 5/04; B65D 25/08
(52) U.S. Cl. ...................... 433/90; 206/220; 222/145.6; 366/602
(58) Field of Search ....................... 433/89, 90; 604/82, 604/87, 88, 89; 222/145.5, 145.6, 202–203, 214; 206/220, 219, 222; 366/602

(56) References Cited
U.S. PATENT DOCUMENTS

| | | | |
|---|---|---|---|
| 2,487,236 A | * | 11/1949 | Greenberg .................. 206/220 |
| 3,451,540 A | | 6/1969 | Kulischenko |
| 3,595,439 A | * | 7/1971 | Newby et al. ................. 222/80 |
| 3,739,947 A | | 6/1973 | Baumann et al. |
| 4,197,943 A | * | 4/1980 | Weikel ....................... 206/219 |
| 4,362,242 A | | 12/1982 | Cheetham |
| 4,863,017 A | | 9/1989 | Vlock |
| 5,392,904 A | | 2/1995 | Frick et al. |

FOREIGN PATENT DOCUMENTS

| | | |
|---|---|---|
| DE | 1 939 316 | 8/1973 |
| DE | 33 03 839 | 8/1984 |
| DE | 36 35 547 | 4/1988 |
| DE | 39 20 537 | 2/1990 |
| DE | G 92 15 748.3 | 3/1993 |
| DE | 43 15 920 | 12/1994 |

OTHER PUBLICATIONS

International Search Report.

* cited by examiner

Primary Examiner—Cary E. O'Connor
(74) Attorney, Agent, or Firm—Crowell & Moring LLP

(57) ABSTRACT

A mixing capsule, especially for the production of dental materials, comprises a cartridge that is closed on one end by a piston. The piston has a hemispherical recess that forms a secondary chamber and is closed off from the main chamber of the cartridge by a separating device. A body that is provided in the initial state in the main chamber is used to facilitate the mixing process and to penetrate the separating device at the beginning of the process, whereby the main chamber and the secondary chamber form a single mixing area. The body preferably disintegrates during the mixing process.

18 Claims, 2 Drawing Sheets

MIXING CAPSULE

BACKGROUND AND SUMMARY OF THE INVENTION

The present invention relates to a mixing capsule and a device containing a mixing capsule, particularly a mixing device and/or an application device, as well as a method for using the mixing capsule, particularly for the preparation of a dental material preferably containing several components.

For the production of mixtures of two or more components, mixing capsules are used, which are filled by the manufacturer with the components in separate chambers. The user combines and mixes the components, for example by destroying a wall separating the chamber.

In the dental area, mixing capsules are known for the production of dental materials that are frequently mixed from a powdery and a liquid component, wherein the mixing process generally takes place in a shaker. The finished mixed substance is then applied directly to the working area, for example a tooth cavity, through an ejection sleeve that is molded to the mixing capsule.

From DE 36 35 574 A we know of a mixing capsule, which is used for the production of joining and sealing masses. In an embodiment described in this document, a secondary chamber that is incorporated in the ejector piston is limited on the side facing the main chamber of the capsule by a foil and on the opposite side by an auxiliary piston that is arranged displaceably in the ejector piston. In the starting position of the mixing capsule, a mixing body is provided in the secondary chamber apart from the second component, wherein this body initially serves to destroy the foil through manual shifting of the auxiliary piston and subsequently supports the mixing process. In order to enable the volume reduction necessary for shifting the inner piston including the ball, a gas cushion is provided in the mixing chamber.

In another embodiment of a known familiar mixing capsule, the mixing ball is initially located in the main chamber. In this case, the secondary chamber existing in the piston is closed off towards the main chamber by a cover and on its rear by a bellows. Through manual pressure on the bellows, the cover is pushed away from the piston so that the two chambers connect and activate the capsule.

In both cases, a step that needs to be performed on its own manually is required to activate the capsule. Furthermore a gas cushion is required in order to enable the volume reduction necessary to loosen the cover.

In a multiple component mixing capsule for dental purposes known from DE 94 00 374 U1, a first component is contained in a mixing chamber and a second, liquid component in a foil bag, which is arranged in a secondary chamber that is separated from the mixing chamber by a sliding wall element. A cylindrical mixing body contained in the mixing chamber serves the purpose of sliding the wall element at the beginning of the mixing process and thus pressing the foil bag together, causing it to burst open and thus releasing the liquid component through a passage for the fluid incorporated in the wall element.

The difficulty with this device is that the wall element, the foil bag and the capsule itself need to be designed in such a way and dimensioned with such tolerance settings that the wall element is held in its original position during storage and transport position of the capsule. But it is shifted under the influence of the mixing body so far and with such force that the foil bag bursts open. It must be taken into consideration that often only a partial emptying of the foil bag leads to undesirable changes to the mixing ratio, and thus to a worsening of the properties of the finished mixture. It is also disadvantageous that this arrangement is only suitable for mixing, but not for applying the paste.

DE 93 03 268 U1 describes a multiple component mixing capsule with an application device for a mixed mass, particularly for dental applications. This mixing capsule contains an activation pin located in the interior of the capsule, wherein this pin is fastened with mountings in the interior of the capsule body against the pressing direction, as well as a fluid compartment arranged in the interior of a stamp, wherein the compartment is sealed against the activation pin with a destructible membrane. The activation pin is fit flush in the empty container in the interior of the die and seals it during the pressing operation. During pressing in the longitudinal direction, fluid reaches the mixing chamber through thin capillaries, which rest in the interior of the activation pin. It is also stated that during the mixing process in a vibratory agitator and during the ejection of the mass through the ejection sleeve always a small, not exactly reproducible fluid residue remains in the capillary. This impairs the quality of the mixing result.

A comparable mixing capsule is described in patent application WO 00/30953. The disadvantage in this mixing capsule is that, upon activation of the capsule, the ball can lead to the development of significant noise. Additionally, the application of force caused by the mixing body can lead to a separation of the separating foil, which can lead to an undesirable contamination of the material that is to be mixed.

Making an improved mixing capsule that avoids the above-mentioned problems without impairing the desired mixing result can be regarded as a primary objective of the invention.

Furthermore, it is the task of the invention to make a device available that permits the mixing and application of multiple component materials in a simple manner.

This task is resolved with a mixing capsule and a method as described in the claims.

The terms "comprise" or "contain" in the sense of the invention introduce a list of features that is not complete. The term "a/one" should be interpreted as an undetermined quantity in the sense of "at least one".

The mixing capsule of the invention exhibits, among other things, the following advantages:

The movable body contained in the mixing capsule serves on one hand for activation of the capsule while destroying the separating device, and, on the other hand, it supports the mixing process.

The fact that the body can change its outward shape during the mixing process continuously decreases noise during the mixing process.

Beyond that, the application of the mixed mass by the mixing body is not impaired, which is beneficial particularly in the application of highly viscous material.

Associated with this is possibly also a reduction of the force that must be generated to apply the mass by sliding the piston.

Through the destruction of the outward shape of the body, additionally the risk of separating the separating device from the piston during the mixing process and of contaminating the mass to be mixed with the separated parts and thus impair the application process is reduced.

A change in the outward shape in the sense of the invention means plastic deformation, surface enlargement, destruction of the outward appearance, pulverization of the body material, integration and/or inclusion of the material that surrounds the body and/or of which the body basically consists in the substance that is to be mixed.

Since the body in the original state is located in the main chamber, activation preferably occurs automatically at the beginning of the mixing process, contrary to the activation types from the state of the art, which are performed manually.

Since the secondary chamber is separated from the main chamber by the separating device to be penetrated by the body, a portion of the mixing chamber is formed on its own during the subsequent mixing process. This way it is ensured that the second component contained in the secondary chamber completely blends with the created mixture.

Additionally, the contamination of main and secondary chambers leads to a beneficial enlargement of the mixing space that is available.

Furthermore, the low quantity and simple design of the components of the mixing capsule are advantageous.

If necessary, several freely movable bodies, which change their outward shape during the mixing process, are located in the mixing capsule.

Preferably, the movable body has a ball shape. The diameter of the ball is preferably in the range of 4 to 10 mm, particularly preferred is the range from 5 to 8 mm. Any other shape of the body however is also conceivable, for example a design in the shape of an ellipsoid, or a configuration with corners and edges, possibly in the shape of a cube. Such a design may destroy the separating layer more easily and may permit a smaller mass and/or size of the body.

The weight of the movable body is adjusted to the characteristics of the separating device in such a way that the separating device is not damaged by the movable body during conventional transport and regular handling processes. It is only beyond acceleration values that generally occur in capsule mixing devices of, for example, 100 to 500 g (1 g=9.81 ms$^{-2}$), preferably 200 to 400 g, that the separating device can be penetrated.

Ball materials that can be used have a density in the range of 1.5 to 9.0 g/cm$^3$, preferably in the range of 2.0 to 6.0 g/cm$^3$. The mass of the body is generally in the range of 0.1 to 2.0 g, preferably in the range of 0.2 to 1.0 g.

For the body in the mixing capsule in particular materials that do not negatively influence the properties of the mixed mass are suited. Such materials are preferably of inorganic nature, possibly of ceramic nature and comprise, e.g., glass, silicon oxide, aluminum oxide, or zirconium oxide.

Contamination of the mixed mass by material from the body can also be avoided by producing the body out of the same material, if necessary comprising it, that is used as the first component in powder and/or granular form in the main chamber of the capsule. The body is preferably produced in a pressing operation from the material of the first component.

It is also conceivable that the main chamber apart from the body contains no additional component, and that all material of the first component that is to be mixed already exists as a body in the pressed state.

Such an embodiment is particularly beneficial if it is to be avoided that the impulse of the body during the mixing process be dampened by the powdery material of the first component contained in the main chamber. This enables possibly a reduction in the weight of the body, which is required to penetrate the partition wall.

Additionally, this embodiment enables a reduction in the size of the mixing capsule, since during the mixing operation the dissolving body becomes a part of the material that is to be mixed and thus does not limit the volume required for the mixing process.

The shape of the secondary chamber may have the shape of a hemisphere with a somewhat larger radius compared to the body. Any other design, for example a cylindrical shape, is also conceivable.

The overall volume of the mixing capsule available for the mixing process is generally in the range of 0.5 to 5 ml, particularly 1 to 3 ml. Preferably, the volume of the secondary chamber is less than the volume of the main chamber. The volume of the secondary chamber is generally 0.05 to 0.5 ml, preferably 0.1 to 0.3 ml.

The mixing capsule according to the invention also does not necessarily require the existence of channel-shaped indentations, which for example can be incorporated in the secondary chamber in the form of grooves and/or into the front wall of the main chamber in the shape of troughs, in order to guarantee application of particularly highly viscous substances from the mixing capsule.

In a particular embodiment, the separating device has at least one rupture joint, which independently of the properties of the peripheral area of the piston contributes to a focused and safe opening of the secondary chamber on the transition to the secondary chamber. Prior damage of the separating device and/or the preparation of a target breakage area can occur for example through radiation, such as laser radiation, mechanically through slitting or cutting with a knife or thermally through melting or perforation with a heated blade.

Preparation occurs preferably only on the possibly existing synthetic part of the separating device, i.e., on the substrate available on one or both sides of a metal layer or SiO$_x$-containing layer. This way the closeness of the possibly existing metal or SiO$_x$-containing layer is maintained.

The preparation method is a matter of choice here, but preferably takes on a form that avoids tearing the separating device or parts thereof after or during penetration of the separating device by the body. A preparation of the separating device in the form of two or more lines intersecting in the axis of symmetry of the capsule has proven favorable.

Useful is also a star-shaped preparation with branching sections. Such a preparation facilitates the mixing process since wedge-shaped foil parts of the separating device in the area of the wall of the secondary chamber have a shorter side length, allowing the foil components to be folded over more easily during the mixing operation.

A preparation in which a foil part has the outline of a bowling pin is also beneficial, wherein the pinhead has a circular design and is located in its center on the longitudinal axis of the cartridge. This preparation facilitates the largely complete opening of the separating device and thus access to the secondary chamber as well.

Suitable preparations of the separating device are shown schematically in FIGS. 3 and 4.

In this case, the separating layer only bursts in a defined location. This avoids that the separating layer or parts thereof reach the mixture and prevent the ejection process.

Another benefit of a target breakage area generated this way consists of the fact that also relatively thick foils, also multi-layer foils in the range of 50 to 80 µm, preferably 60 to 70 µm, can be penetrated with little force (smaller mass of the body).

The separating device preferably sticks to a ring surface of the piston limiting the secondary chamber. The transition between the ring surface and the interior wall of the secondary chamber may have a sharp-edged area.

This sharp-edged area extends preferably across a section of the periphery, preferably basically from 60° to 120°, particularly preferred from 70° to 90°. The transition between the ring surface and the interior wall of the secondary chamber is preferably rounded off in the remaining area. This embodiment avoids that the foil is torn off completely.

The separation device preferably exists in the form of a single- or multi-layer foil, particularly preferred in the form of a sandwich foil or also a sealant foil. The foil preferably comprises at least one metal layer, such as an aluminum layer and/or gold layer, and at least one, possible two, three or more, plastic layers. A three-layer foil, comprising a plastic outer layer, at least one barrier layer, preferably made of resin, and a sealant layer, has proven beneficial, wherein the sealant layer can also be a synthetic foil or a sealant paint.

Furthermore, the separating device can contain plated or other resin barrier layers, plasma polymerized layers such as hydrocarbon containing layers, or ceramic barrier layers such as $SiO_x$ layers instead of or in addition to the metal foil.

The separating device is fastened to the circular-shaped end face of the piston, for example, through heat sealing, gluing, ultrasound welding, or high frequency welding.

Layers comprising PET, PP, PE, PTFE, PVC and/or PA are suitable, for example, for the outer layer, layers comprising Al, $SiO_x$, PVDC and/or EVOH for the blocking layer, layers comprising HDPE, LDPE and/or PP for the sealant layer. A PET-Al-LDPE or PA-Al-LDPE coating has proven useful.

The layer thickness of the individual foils (outer layer, blocking layer, sealant layer) is in the range of 5 to 60 $\mu$m, preferably from 8 to 50 $\mu$m.

The separating device can furthermore be designed to hold a third component, for example in the form of a foil cushion.

Beneficial materials for the piston of the mixing capsule comprise metals such as anodized aluminum, titanium, and iron-containing materials such as steel sheets and synthetics. In order to reduce the permeability of synthetic-containing pistons towards liquids and gases, such a piston may contain plated materials or synthetics vaporized or coated with other materials that have a blocking layer effect. Synthetics that are possible include PE, PP, PET, PTFE, PVC, and polyamides.

Furthermore, combinations of the above-mentioned materials, such as a metal insert, preferably made of aluminum or steel, are feasible, surrounded on the inside and outside with the synthetic. Such parts can be produced in an injection molding procedure. Production through thermo-forming and/or deep-drawing of e.g. aluminum composite foils or resin-coated steel metal sheets is also conceivable.

The piston can be manufactured in a 2-component injection molding procedure. For this, initially an inlay is produced, which is subsequently surrounded with, e.g., PE.

Application of the mixed mass from the mixing capsule generally occurs through the use of a suitable application device. Such a device usually contains a die, which moves the piston of the mixing capsule in the direction of the application orifice via lever action.

If a nearly complete emptying of the mixing capsule is to be ensured, dead space must be avoided. Such dead space can present a problem particularly with highly viscous masses, and have a disadvantageous effect when the overall volume of the mixed mass is small compared to the volume of the dead space.

If the dead space is to be kept as small as possible, it is beneficial when no additional indentations (for example, in the shape of a trough), are embedded in the pistons and/or the front wall of the main chamber.

The piston is preferably designed such that it can be subjected to deformation during the application process, in particular to plastic deformation. The deformation preferably occurs in such a way that the piston adapts to the shape exhibited by the mixing capsule at the end on which the ejection sleeve is located.

This can be accomplished by ensuring that the piston, which contains at least one secondary chamber, consists of a ductile material, or comprises such a material.

A design in such a geometric shape that facilitates such deformation is also useful.

It has also proven favorable to use a design of the piston in the form of a tubular piston that is open on two sides, with a first and a second recess, wherein the first recess together with the separating device forms the secondary chamber.

Such a form can be attained, for example, by pressing in the bottom surface of a cup consisting of a deformable material. Pressing preferably occurs with a die, in particular a hemispherical die.

It is also conceivable to produce such a piston through molding or deep-drawing and/or thermo-forming of a ductile material.

To ensure that the piston is better sealed against the capsule wall, the piston preferably contains one or more sealing lips.

An additional sealing effect can be accomplished by a design th at permits an expansion of the collapsing piston during the application process, associated with a pressing against the capsule wall.

If necessary, the escape of volatile substances, which are located in particular in the secondary chamber of the mixing capsule, can be prevented through the application of a sealant foil onto the bottom-side opening of the mixing capsule into which the piston is introduced.

The combination of ductile pistons and mixing bodies whose outward shape is destroyed during the mixing process and/or which is incorporated during the mixing process into the mass that is to be mixed is particularly beneficial when a nearly complete ejection of the mixed mass is to be ensured.

In order to ensure complete ejection of the mixture from the mixing capsule, it may also be beneficial to attach a molded part to the outer side of the piston bottom. Such a molded part can take on the shape of a thickening of the piston bottom or a distance piece, preferably in cylindrical shape. Since for the ejection of the mixture an application device is required, which has a movable piston rod or a die with a defined length that is standardized for the market, it may become necessary to extend the axial length of the die via the molded part. This way, it can be assured that the ductile piston can be shifted all the way to the ejection sleeve. Furthermore it is beneficial that the risk for the piston rod or the die of the application device to become stuck during deformation of the piston of the mixing capsule is thus reduced.

The components contained in the main chamber, the secondary chamber and/or possibly in the separating device comprise both fluids and solid matters, preferably in powder form. However paste-like basic substances are also possible.

The solid matter comprises inert fillers, such as finely ground quartz, $SiO_x$-containing substances, glass, and reactive fillers of all kinds, wherein the solid matter may exist in a surface-modified way.

The fluids comprise, in particular, matrix-forming, polymerizable substances, for example polyacids, comprising acrylic acid, methacrylic acid, and maleic acid derivatives as well as copolymers thereof.

The mixing capsule is preferably suited for storing, mixing and applying glass ionomer cements.

The ejection sleeve on the mixing capsule preferably attaches in a coaxial, possibly also in an eccentric manner to the main chamber.

The ejection sleeve furthermore has a closable design. Feasible embodiments are described, for example, in EP 0 157 121 A, where the ejection sleeve is seated in a swiveling manner so that depending on the position of the ejection sleeve that spout is closed or opened. Also feasible is the use of a blowpipe displacement cap for closing the ejection sleeve.

The mixing capsule may contain coding. Suitable codings are, for example, color markings, such as in the form of color rings, labels, imprints or electronically legible codings (bar codes). It is also feasible that several codings are applied. The coding can contain information about the mixing time, the material, the manufacturer and/or the expiration date. Coding can also occur through the coloration of a mixing capsule component, preferably the sleeve.

A coding of the mixing capsule or the substances found therein through a colored design of the ejection sleeve is particularly advantageous when photo-sensitive substances are to be stored in the mixing capsule. In order to protect them from incident light, it is often necessary to color the piston and/or the cartridge black. If substances of differing colors are to be stored in the cartridge, identification of these substances can no longer occur through the color of the now black piston and/or cartridge.

The object of the invention is also a method for mixing and applying mixtures from mixing capsules, including the following steps:

a) making a mixing capsule available with at least two chambers in which components of the mixture are stored separately from each other, separated by a separating device, comprising a cartridge, a piston that is arranged displaceably in the cartridge, an ejection sleeve and at least one freely movable body that can penetrate the separating device, b) inserting the mixing capsule in a mixing device with a capsule holder, c) accelerating the mixing capsule preferably through rapid translatory and/or rotatory movements, wherein the at least two chambers that are separated by a separating device are opened while forming a mixing chamber, d) removing the mixing capsule from the mixing device, and e) sliding the piston while utilizing an application device with a piston rod, wherein the mixture created in c) is introduced into or removed from a surface, especially dental hard tissue or a tooth cavity, via the ejection sleeve of the mixing capsule.

A conventional application device comprises a mounting for inserting the mixing capsule and a sliding piston rod that is dimensioned such that it can move the piston of the mixing capsule in the direction of the ejection opening.

Preferred embodiments of the mixing capsule are explained in the following based on the drawings.

DETAILED DESCRIPTION OF THE DRAWINGS

Figure 1:
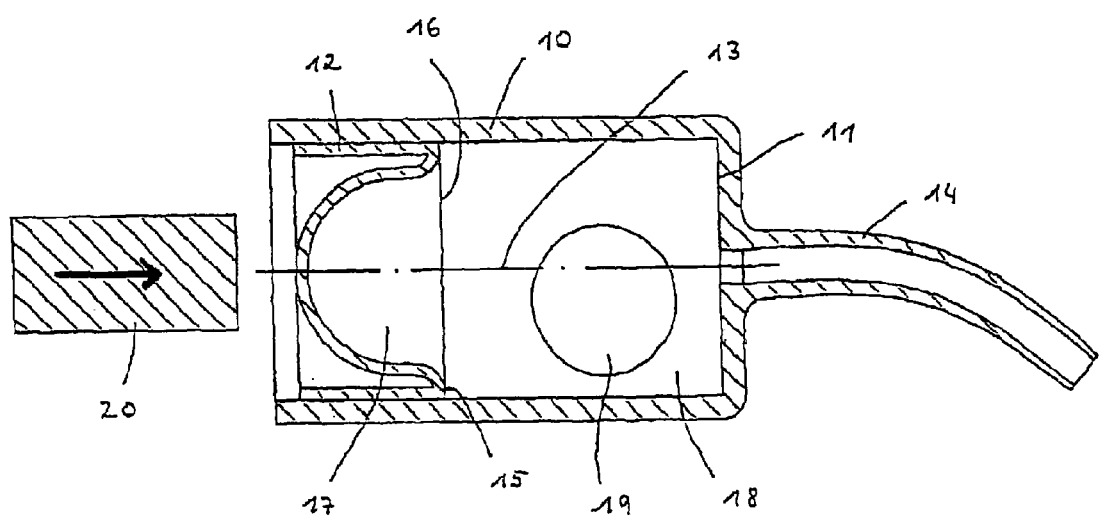
FIG. 1 shows a longitudinal section through a mixing capsule in the initial state.

According to FIG. 1, the mixing capsule comprises a cylindrical cartridge 10, which on its front end is closed by a front wall 11 and on its rear end by a piston 12. On the front wall 11 an arched ejection sleeve 14 is molded on coaxially to the cartridge axis 13. The ejection sleeve 14 can be designed in a locking manner, for example with a displacement plug.

The piston 12 is equipped with an indentation that is coaxial to the cartridge axis 13, with this indentation being closed by a separating device 16 that is fastened to the ring-shaped front end face 15 of the piston 12. The separating device 16 separates the secondary chamber 17 formed by the indentation from the remaining interior of the cartridge, which is called the main chamber 18 here. The piston 12 possesses another coaxial indentation on the side opposite the secondary chamber, wherein this indentation is adjusted to the shape of the secondary chamber.

In the original and/or storage state, the main chamber 18 may possibly contain a first, for example, powdery and/or granular component and the secondary chamber 17 a second, for example, liquid component of the mixture that is to be prepared.

The mixing capsule furthermore contains a freely movable, possibly ball-shaped body 19, which, in the original and/or storage state of the capsule, is located in the main chamber 18 and whose radius is preferably somewhat smaller than the radius of the indentation forming the secondary chamber 17. The body 19 and the secondary chamber 17 can take on other shapes deviating from a ball or hemispherical shape. Freely movable means that the body can basically move in all directions and is not impaired by any guiding rails in its movement.

The transition between the indentation forming the secondary chamber 17 and the preferably ring-shaped end face 15 of the piston 12 is preferably rounded off, however can also have sharp edges through an angled area. The sharp edges can also be generated through a toothed section. The rounded-off area prevents the separating device from rupturing in this end face interior edge area during the mixing process.

When the edge of the secondary chamber 17 is rounded all the way, the separating device 16 can be ruptured by overextending it through the impact of the body 19 at the beginning of the mixing process preferably in the rupture joint.

For applications, the mixing capsule, which is supplied by the manufacturer in the state depicted in FIG. 1, is generally inserted into a conventional capsule mixing device, where it is brought to oscillation, for example along the cartridge axis 13. Apart from purely translatory movements of the capsule, rotatory movements are possible, if necessary in combination with translatory movements. The body 19 then meets with the separating device 16 and penetrates it. This causes the main chamber 18 and the secondary chamber 17 to be combined to a joint mixing chamber. In this mixing chamber, the components are blended during the continued mixing process. During the mixing operation the body 19 disintegrates and is embedded, preferably worked, into the mass that is being mixed.

Figure 2:
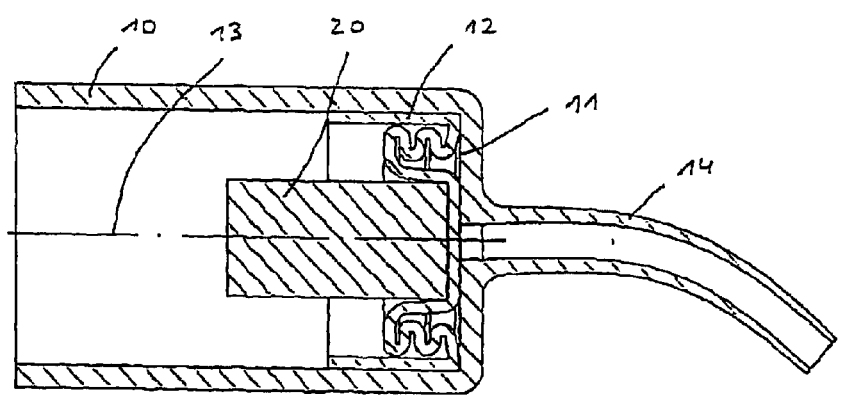
FIG. 2 shows the same capsule at the end of the ejection process.

For ejection of the finished mixture, the piston 12 is shifted forward in a conventional application instrument with a die 20 until it has reached the position shown in FIG. 2, dependent upon the material properties of the piston, and preferably no longer has a secondary chamber.

The deformation preferably occurs with the simultaneous reduction in volume of the secondary chamber only when the ring surface 15 of the piston 12 has come to rest against the front wall of the cartridge. This can be achieved for example by ensuring that the frictional force between the piston and the interior cartridge wall is lower than the force that must be applied to deform the piston.

Figure 3:
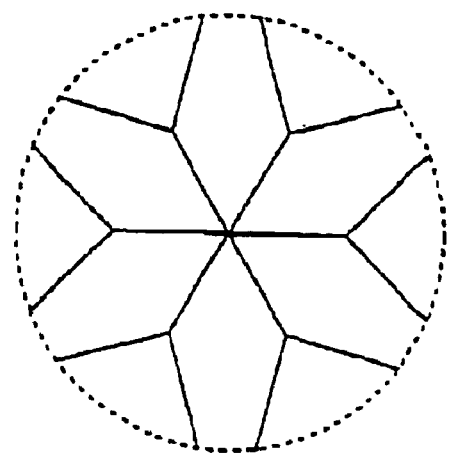
FIG. 3 shows possible preparations of the separating device in top view.
Figure 4:
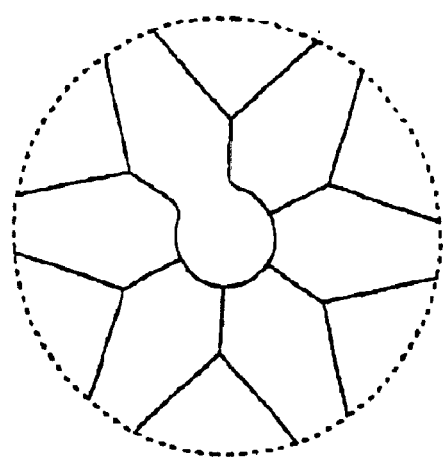
FIG. 4 shows a top view of a preparation of the separating device.

FIGS. 3 and 4 show a top view of possible preparations of the separating device 16, which enable the mixing capsule to be activated in a simple and largely complete manner, without embedding components of the separating device in the mixed mass during the mixing operation. Preparation preferably occurs by previously damaging the foil used as the separating device, for example through radiation.

The mixing capsule is generally used together with another device. Device, in the sense of the invention, should be interpreted on one hand as an apparatus that is used to activate the mixing capsule, preferably an apparatus that can cause the mixing capsule to perform translatory and/or rotatory movements, and on the other hand as an apparatus that facilitates the application of the mixed mass from the mixing capsule, preferable a device comprising a die and/or a sliding piston rod.

What is claimed is:

1. A mixing capsule, comprising:
    a first end;
    an ejection sleeve in fluid communication with said first end;
    a second end opposite said first end and defined by a piston;
    a separating device disposed between said first and second end;
    a main chamber disposed between said first end and said separating device;
    a secondary chamber disposed between said second end and said separating device;
    at least one body provided in said main chamber;
    a first component provided in said main chamber; and
    a second component provided in said second chamber,
    wherein said piston comprises a deformable material;
    wherein said at least one body can penetrate said separating device; and
    wherein said at least one body has an outward shape which changes during use of the mixing capsule.

2. A mixing capsule according to claim 1, wherein said outward shape of said at least one body is selected from the group consisting of spherical, ellipsoid and angular.

3. A mixing capsule according to claim 1, wherein said first component comprises said at least one body.

4. A mixing capsule according to claim 1, wherein said separating device is subjected to a preparation process prior to use to form at least one rupture joint.

5. A mixing capsule according to claim 4, wherein said rupture joint forms a shape selected from the group consisting of star-shaped, branched in a star-shaped pattern, and cone-shaped.

6. A mixing capsule according to claim 1, wherein a frictional force between said piston and an exterior wall defining said main chamber is less than a deforming force required to deform said piston.

7. A mixing capsule according to claim 1, wherein said deformable material of said piston comprises at least one of metals or synthetics.

8. A mixing capsule according to claim 1, wherein said piston is tubular and comprises coaxial indentations on two sides.

9. A mixing capsule according to claim 1, wherein said separating device comprises at least one item selected from the group consisting of a metal-containing foil, a hydrocarbon-containing layer, and a ceramic barrier layer.

10. A mixing capsule according to claim 9, wherein said ceramic barrier layer comprises $SiO_x$.

11. A method of mixing a dental material, comprising:
    providing components of a dental material in a mixing capsule according to claim 1; and
    accelerating said mixing capsule.

12. A method of using a mixing capsule, comprising:
    inserting the mixing capsule into a capsule holder of a mixing device;
    accelerating the mixing capsule through at least one of translatory movement and rotatory movement;
    removing the mixing capsule from said mixing device; and
    releasing at least one content of said mixing capsule,
    wherein said mixing capsule comprises a cartridge separated into at least two chambers by a separating device, at least one freely movable body capable of penetrating said separating device, an ejection sleeve in fluid communication with said cartridge, and a piston displaceably disposed in said cartridge; and
    wherein said at least one content of said mixing capsule is released by displacing said piston to force said at least one content out of said cartridge through said ejection sleeve.

13. A method of using a mixing capsule according to claim 12, wherein a first dental material component is disposed in a first chamber of said mixing capsule, and a second dental material component is disposed in a second chamber of said mixing capsule.

14. A method of using a mixing capsule according to claim 13, wherein said first dental material component comprises said at least one freely movable body.

15. A method of using a mixing capsule according to claim 12, wherein said piston is deformable.

16. A method of using a mixing capsule according to claim 15, wherein a frictional force between said piston and said cartridge is less than a force required to deform said deformable piston.

17. A method of making a mixing capsule for a dental material, comprising:
    forming a main chamber and a secondary chamber separated by a separating device;
    providing a first component in said main chamber;
    providing a second component in said secondary chamber;
    providing at least one body in said main chamber,
    wherein a portion of said second chamber not defined by said separating device comprises a deformable piston; and wherein said at least one body is configured to penetrate said separating device.

18. A method of using a mixing capsule, comprising:

providing a body comprising a first component of a dental material in a main chamber of a mixing capsule;

providing a second component of a dental material in a secondary chamber of said mixing capsule, which secondary chamber is defined in part by a deformable piston;

providing a separating device between said main chamber and said secondary chamber, said separating device defining portions of the secondary chamber not defined by the deformable piston;

placing said mixing capsule in a mixing device; and accelerating said mixing capsule with consequent movement of said body to penetrate said separating device.

* * * * *

UNITED STATES PATENT AND TRADEMARK OFFICE
CERTIFICATE OF CORRECTION

PATENT NO. : 6,884,071 B2 Page 1 of 1
APPLICATION NO. : 10/204246
DATED : April 26, 2005
INVENTOR(S) : Martin Mathias It is certified that error appears in the above-identified patent and that said Letters Patent is hereby corrected as shown below:

<u>On the Title Page, [54]</u>
After "CAPSULE" insert -- AND METHOD OF USING AND MAKING SAME --.

<u>Column 1</u>
Line 1, after "CAPSULE" insert -- AND METHOD OF USING AND MAKING SAME --.

<u>Column 3</u>
Line 39, delete "1 g" and insert -- 1g --, therefor.

<u>Column 6</u>
Line 37, delete "th at" and insert -- that --, therefor.

Signed and Sealed this

Eighteenth Day of November, 2008

JON W. DUDAS
*Director of the United States Patent and Trademark Office*